United States Patent [19]

Devries et al.

[11] Patent Number: 4,731,498

[45] Date of Patent: Mar. 15, 1988

[54] ENHANCING THE PRODUCTION OF HIGHER MOLECULAR WEIGHT HYDROCARBONS FROM LOWER MOLECULAR WEIGHT HYDROCARBONS BY THE ADDITIONS OF ALUMINUM VAPOR TO THE FEED

[75] Inventors: Louis Devries, Greenbrae; P. R. Ryason, Santa Rosa, both of Calif.

[73] Assignee: Chevron Research Company, San Francisco, Calif.

[21] Appl. No.: 879,665

[22] Filed: Jun. 27, 1986

[51] Int. Cl.$^4$ .............................................. C07C 2/00
[52] U.S. Cl. .................................. 585/415; 585/417; 585/418; 585/500; 585/541; 585/654; 585/656; 585/700; 585/943
[58] Field of Search ............... 585/415, 417, 500, 654, 585/656, 943, 700

[56] References Cited

U.S. PATENT DOCUMENTS

| | | | |
|---|---|---|---|
| 1,801,382 | 4/1931 | Wutzel | 585/943 |
| 1,917,627 | 7/1933 | Wulff | 585/943 |
| 1,965,770 | 7/1934 | Burgin | 585/943 |
| 2,022,279 | 11/1935 | Feiler | 585/943 |
| 2,608,594 | 8/1952 | Robinson | 585/943 |
| 4,172,810 | 10/1979 | Mitchell, III et al. | 585/943 |
| 4,465,893 | 8/1984 | Olah | 585/500 |
| 4,507,517 | 3/1985 | Devries et al. | 585/500 |

FOREIGN PATENT DOCUMENTS 2148935 6/1985 United Kingdom ............... 585/500

*Primary Examiner*—William R. Dixon, Jr.
*Assistant Examiner*—Cynthia A. Prezlock
*Attorney, Agent, or Firm*—S. R. LaPaglia; R. C. Gaffney; J. J. DeYoung

[57] ABSTRACT

In a continuous catalytic process for the production of higher molecular weight hydrocarbons from lower molecular weight hydrocarbons in which a lower molecular weight hydrocarbon containing reaction gas is contacted in a reaction zone with a higher molecular weight hydrocarbon synthesis catalyst under $C_2+$ hydrocarbon synthesis conditions, the improvement comprising increasing the production of higher molecular weight hydrocarbons by the addition of an effective amount of aluminum metal vapor to the reaction gas, said synthesis conditions including a temperature greater than 1000° C. and a gas hourly space velocity of greater than 3200 hr$^{-1}$.

22 Claims, No Drawings

ENHANCING THE PRODUCTION OF HIGHER MOLECULAR WEIGHT HYDROCARBONS FROM LOWER MOLECULAR WEIGHT HYDROCARBONS BY THE ADDITIONS OF ALUMINUM VAPOR TO THE FEED

FIELD OF THE INVENTION

The present invention relates to a catalytic process for the production of higher molecular weight hydrocarbons from lower molecular weight hydrocarbons. More particularly, the present invention is concerned with increasing the production of higher molecular weight hydrocarbons in a catalytic methane conversion process by the addition of aluminum vapor to the reaction gas.

BACKGROUND OF THE INVENTION

It is the business of many refineries and chemical plants to obtain, process and upgrade relatively low value hydrocarbons to more valuable feeds, or chemical raw materials. For example, methane, the simplest of the saturated hydrocarbons, is often available in rather large quantities either as an undesirable by product in admixture with other more valuable higher molecular weight hydrocarbons, or as a component of an off gas from a process unit, or units. Though methane is useful in some chemical reactions, e.g., as a reactant in the commercial production of methanol and formaldehyde, it is not as useful a chemical raw material as most of the higher molecular weight hydrocarbons. For this reason process streams which contain methane are usually burned as fuel Methane is also the principal component of natural gas, which is composed of an admixture of normally gaseous hydrocarbons ranging $C_4$ and lighter and consists principally of methane admixed with ethane, propane, butane and other saturated, and some unsaturated hydrocarbons. Natural gas is produced in considerable quantities in oil and gas fields, often at remote locations and in difficult terrains, e.g., offshore sites, arctic sites, swamps, deserts and the like. Under such circumstances the natural gas is often flared while the oil is recovered, or the gas is shut in, if the field is too remote for the gas to be recovered on a commercial basis. The construction of pipelines to carry the gas is often not economical, due particularly to the costs of connecting numerous well sites with a main line. Transport of natural gas under such circumstances is also uneconomical because methane at atmospheric pressure boils at $-258°$ F. and transportation economics dictate that the gas be liquefiable at substantially atmospheric pressures to reduce its volume. Even though natural gas contains components higher boiling than methane, and such mixtures can be liquefied at somewhat higher temperatures than pure methane, the temperatures required for condensation of the admixture is nonetheless too low for natural gas to be liquefied and shipped economically. Under these circumstances the natural gas, or methane, is not even of sufficient value for use as fuel, and it is wasted.

The thought of utilizing methane from these sources, particularly avoiding the tremendous and absolute waste of a natural resource in this manner, has challenged many minds, but has produced few solutions. It is highly desirable to convert methane to hydrocarbons of higher molecular weight (hereinafter, $C_2+$) than methane, particularly admixtures of $C_2+$ hydrocarbon products which can be economically liquefied at remote sites; especially admixtures of $C_2+$ hydrocarbons rich in ethylene or benzene, or both. Ethylene and benzene are known to be particularly valuable chemical raw materials for use in the petroleum, petrochemical, pharmaceutical, plastics and heavy chemicals industries. Ethylene is thus useful for the production of ethyl and ethylene compounds including ethyl alcohol, ethyl ethers, ethylbenzene, styrene, polyethylbenzenes ethylene oxide, ethylene dichloride, ethylene dibromide, acetic acid, oligomers and polymers and the like. Benzene is useful in the production of ethylbenzene, styrene, and numerous other alkyl aromatics which are suitable as chemical and pharmaceutical intermediates, or suitable in themselves as end products, e.g., as solvents or high octane gasoline components.

It has been long known that methane, and natural gas can be pyrolytically converted to $C_2+$ hydrocarbons. For example, methane or natural gas passed through a porcelain tube at moderate red heat will produce ethylene and its more condensed homologs such as propylene, as well as small amounts of acetylene and ethane. Methane and natural gas have also been pyrolytically converted to benzene, the benzene usually appearing in measurable quantities at temperatures above about $1650°$ F. ($899°$ C.), and perhaps in quantities as high as 6–10 wt. % at $2200°$ F. to $2375°$ F., ($1204°$ to $1302°$ C.) or higher. Acetylene and benzene in admixture with other hydrocarbons, have been produced from methane and natural gas in arc processes, cracking processes, or partial combustion processes at temperatures ranging above about $2775°$ F. ($1524°$ C.). Heat for such reactions has been supplied from various sources including electrically heated tubes, electric resistance elements, and spark or arc electric discharges. These processes characteristically require considerable heat energy which, most often, is obtained from combustion of the by-product gases. The extreme temperatures coupled with the low yields of higher molecular weight hydrocarbons such as benzene an other aromatics have made the operation of such pyrolytic processes uneconomical.

High temperature, noncatalytic, thermal pyrolysis processes involving the conversion of methane in the presence of ethane and other hydrocarbons are well known in the art. Representative articles include: Roczniki Chemi, An. Soc. Chim. Polonorum, 51, 1183 (1977), "The Influence of Ethane on Thermal Decomposition of Methane Studied By The Radio Chromatographic Pulse Technique"; J. Soc. Chem. Ind. (Trans. and Comm.) 1939,58, 323–7; and J. Chin. Chem. Soc. (Taipei) 1983, 30(3), 179–83.

Addition of hydrogen to pyrolysis reaction mixtures is well known, see for example, pp 84–85 in "Pyrolysis Theory and Industrial Practice", L. F. Albright, B. Z. Crynes and W. H. Covcovan (Ed), Academic Press (1983).

Partial oxidation processes of converting methane to $C_2+$ hydrocarbons are well known. In these processes, hydrogen must be removed either as water, molecular hydrogen or other hydrogen-containing species. Likewise, any other polymerization mechanism wherein methane is converted to $C_2+$ hydrocarbon products requires a tremendous amount of energy, most often supplied as heat, to provide the driving force for the reactions. In the past the molecular hydrogen liberated by the reaction has often been separated and burned to provide the necessary process heat. This route has proven an abomination to the production of $C_2+$ hydrocarbons, but alternate reaction pathways have appeared little better, if any, for these have resulted in the production of large quantities of the higher, less useful hydrogen deficient polymeric materials such as coke, and highly oxidized products such as carbon dioxide and water.

Typical of low temperature prior art oxidation processes are those disclosed in U.S. Pat. Nos. 4,239,658, 4,205,194 and 4,172,180 which use a regenerable catalystreagent. U.S. Pat. No. 4,239,658, for example, teaches a process for the conversion of methane to higher molecular weight hydrocarbons. In the process, a three component catalyst-reagent is utilized which comprises a mixture of various metals and metal oxides, particularly a Group VIII noble metal, nickel or a Group VI-B noble metal, a Group VI-B metal oxide and a Group II-A metal. The patent teaches process temperatures from about 1150° to 1600° F. (621° to 871° C.), preferably 1250° F. to about 1350° F. (677° to 732° C.).

It has also been reported in Science 153, 1393, (1966), "High Temperature Synthesis of Aromatic Hydrocarbons From Methane", that aromatic hydrocarbons can be prepared from methane by contact with silica at 1000° C. (1832° F.). The yield of hydrocarbons was in the range of 4.8 to 7.2 percent based on the methane used in a single pass at a space velocity of 1224 $hr^{-1}$.

In the J. Chinese Chem. Soc., Volume 29, pages 263-273 (1981), it is reported that methane can be converted to $C_{2+}$ hydrocarbons at temperatures of 800 to 1130° C. and space velocities of 3100 $hr^{-1}$ or less using a metal oxide catalyst. However, the total conversion of methane, at best, is 7.5 mole percent using a thorium oxide catalyst.

Franz Fischer, reports in an article entitled: "The Synthesis of Benzol Hydrocarbons From Methane At Ordinary Pressure and Without Catalyst" (Brennstoff-Chemie, Vol. 9, pp. 309-316, 1928) that methane is converted to benzol hydrocarbons by passing methane through a hot tube. In carrying out this work Fischer tested many substances for catalytic activity at temperatures ranging from 650° to 1150° C. and at high flow rates and concluded that the substances tested were not catalytic and not necessary. Among the substances tested were elemental iron, copper, tungsten, molybdenum, tin and carbon; and the compounds potassium hydroxide and silica gel.

SUMMARY OF THE INVENTION

In a continuous catalytic process for the production of higher molecular weight hydrocarbons from lower molecular weight hydrocarbons in which a lower molecular weight hydrocarbon containing reaction gas is contacted in a reaction zone with a higher molecular weight hydrocarbon synthesis catalyst under $C_{2+}$ hydrocarbon synthesis conditions, the improvement comprising increasing the yield of higher molecular weight hydrocarbons by the addition of an effective amount of aluminum vapor to the reaction gas, said synthesis conditions including a temperature greater than 1000° C. and a gas hourly space velocity of greater than 3200 $hr^{-1}$.

DETAILED DESCRIPTION OF THE INVENTION

It has been found in the present invention that in the catalytic conversion of lower molecular weight hydrocarbons to higher molecular weight hydrocarbons that the yield of higher molecular weight hydrocarbons is dramatically increased by the addition of a small amount of aluminum vapor to the feed gas.

As used in the present invention the phrase "lower molecular weight hydrocarbons" means hydrocarbons containing at least one or more carbon atoms, i.e., methane, ethane, propane, etc. Also as used in the present invention, the phrase "higher molecular weight hydrocarbons" means hydrocarbons containing two or more carbon atoms and at least one carbon atom more than the lower molecular weight hydrocarbon in the feedstock.

As used herein the phrase "$C_{2+}$ hydrocarbon synthesis conditions" refers to the selection of feedstock, reaction temperature, space velocity and catalyst described hereafter such that higher molecular weight hydrocarbons are produced in the process with yields as described hereafter. Other process parameters necessary to maintain $C_{2+}$ hydrocarbon synthesis conditions, such as the selection of particular types of reaction vessels, etc., is readily determined by any person skilled in the art.

As used in the present invention the word "metal" refers to all those elements of the periodic table which are not non-metals. "Non-metals" for the purpose of the present invention refers to those elements having atomic numbers 1, 2, 5 through 10, 14 through 18, 33 through 36, 52 through 54, 85 and 86.

The word "catalyst" is used in the present invention to mean a substance which strongly affects the rate of a chemical reaction but which itself undergoes no chemical change although it may be altered physically by chemically absorbed molecules of the reactants and reaction products.

As used in the present invention the phrase "continuous catalytic process" means a process in which feedstock and products are simultaneously fed to and removed from a reaction zone containing a catalyst.

As used in the present invention the phrase "reaction gas" refers to the gas or gas mixture being fed to the catalyst-containing reaction zone.

The Reaction Gas and Products

The reaction gas of the present invention will comprise lower molecular weight hydrocarbons and sufficient added aluminum vapor to significantly increase the yield of higher molecular weight hydrocarbons. The lower molecular weight hydrocarbon will comprise methane or natural gas containing $C_1$ to $C_4$ hydrocarbons.

Generally enough aluminum vapor is added to increase the yield of higher molecular weight hydrocarbons by at least 1 weight percent and preferably 3 to 25 weight percent or more as compared to the higher molecular weight hydrocarbons produced from a reaction gas consisting of 100% methane without any added aluminum vapor. Generally, an effective amount of the aluminum metal vapor is added so that the reaction gas comprises 0.01 to 110 parts per million aluminum metal vapor. Preferably, the added aluminum metal vapor comprises 0.02 to 0.5 parts per million and more preferably 0.03 to 0.1 parts per million.

The metal vapor is added by conventional means which are well known in the art. One means is to utilize a bed of metal shavings and pass a small amount of heated gas over the aluminum shavings to vaporize a sufficient amount of the solid metal to provide an effective concentration of the aluminum metal vapor in the reaction zone. Another means is to inject solid or particulate aluminum into the reaction zone, for example, by feeding an aluminum wire into the reaction zone.

The reaction gas can also contain other nonhydrocarbon gases such as nitrogen and hydrogen.

Preferably the reaction gas is essentially free of oxygen-containing or oxygen-forming gases since it is believed that oxygen diminishes the effect of the added aluminum vapor. Such gases include oxygen, water, carbon dioxide, carbon monoxide, etc. By "essentially free" it is meant less than 10 parts per million by weight.

The product higher molecular weight hydrocarbons will comprise $C_2+$ hydrocarbons, particularly mixtures of $C_2+$ hydrocarbons which can be economically liquefied. Preferably, the higher molecular weight hydrocarbon product streams will be rich in ethylene or aromatics such as benzene, or both. The product stream will also contain copious amounts of hydrogen.

The process of the present invention affords high conversions of the lower molecular weight hydrocarbons with high selectivity to higher molecular weight hydrocarbons. More particularly, as measured by the disappearance of the lower molecular weight hydrocarbons, the process of the present invention affords conversions of 19 mole percent or more of the lower molecular weight hydrocarbons, and preferably, the conversions are greater than 25 mole percent and more preferably greater than 40 mole percent. The carbon-containing reaction products comprise 80 mole percent or more of higher molecular weight hydrocarbons, preferably, greater than 90 mole percent. Based on the feed, at least 15 mole percent, and preferably at least 20 mole percent, and more preferably at least 40 mole percent of the lower molecular weight hydrocarbons is converted to higher molecular weight hydrocarbons which is referred to herein as selectivity.

Process Conditions

It is essential to the process of the present invention that a high temperature greater than 1000° C. is maintained in the reaction zone along with a high gas hourly space velocity of greater than 3200 $hr^{-1}$. Preferably, the temperature will be greater than 1100° C. with a space velocity greater than 6000 $hr^{-1}$. Still more preferably the temperature is greater than 1150° C. with a space velocity greater than 9000 $hr^{-1}$.

Generally, the temperature will be in the range of 1001° to 1300° C. while the gas hourly space velocity is in the range 3200 to 360,000 $hr^{-1}$. Preferably, the temperature is in the range 1100° to 1200° C. with a gas hourly space velocity of 6,000 to 36,000 $hr^{-1}$. More preferably the temperature is in the range 1150° to 1175° C. with a gas hourly space velocity in the range of 9,000 to 18,000 $hr^{-1}$. Generally, high temperatures are used with high space velocities and low temperatures are used with low space velocities.

The process can be operated at sub-atmospheric, atmospheric, or supra atmospheric pressure to react and form the higher molecular weight $C_2+$ hydrocarbons. It is preferred to operate at atmospheric pressure or within about 15 psi of atmospheric pressure.

The Catalysts

The lower molecular weight hydrocarbons is introduced into a reaction zone containing a suitable hydrocarbon synthesis catalyst. The reaction-zone catalyst system can be either of the fixed bed type or fluid bed type and the lower molecular weight hydrocarbons can be introduced into the top or bottom of the reaction zone with the product stream removed from either the top or bottom. Preferably, a fixed bed catalyst system is used and the feed stream is introduced into the top of the reaction zone and product is withdrawn from the bottom.

A wide range of catalysts can be used in the present invention. Many commercially available catalysts which have been used in different processes are suitable for use in the process of the present invention. The word "catalyst" is used in the present invention to mean a substance which strongly affects the rate of a chemical reaction but which itself undergoes no chemical change although it may be altered physically by chemically absorbed molecules of the reactants and reaction products. It is also understood that the catalyst of the present invention may be formed in situ. For example, in the present invention when an oxide, nitride, or carbide metal catalyst is initially charged to the reactor, the oxide and nitride may be converted in situ to the carbide which then functions as the catalytic species.

Catalysts useful in the present invention may be used with and without catalyst supports. However, it is generally preferred to use a catalyst support such as the well known aluminas.

The catalysts useful in the present invention may have a wide range of surface areas as measured by the BET method using krypton [Jour. Am. Chem. Soc., vol. 60, pp 309 (1938)]. Low surface areas are preferred. Generally, the catalyst will have a surface area in the range 0.1 to 10 $m^2$/gram, preferably in the range 0.2 to 2.0 $m^2$/gram.

The hydrocarbon synthesis catalysts useful in the present invention will provide conversion of at least 19% of the lower molecular weight hydrocarbons and will maintain this conversion for at least 3 hours under the temperature and space velocity conditions previously discussed. Preferred catalysts of the present invention will provide conversions of 30% or more of the lower molecular weight hydrocarbons feed and remain active for 3 hours or more.

Particularly preferred catalysts are those described in our copending application entitled "Conversion of Low Molecular Weight Hydrocarbons to Higher Molecular Weight Hydrocarbons Using a Metal-containing Catalyst", Ser. No. 547,699, filed Oct. 31, 1983, the entire disclosure of which is incorporated herein by reference. A useful silicon-containing catalyst is described in U.S. Pat. No. 4,567,331, the disclosure of which is incorporated herein by reference. A useful boron compound containing catalyst is described in U.S. Pat. No. 4,507,517, the disclosure of which is incorporated herein by reference.

The hydrocarbon synthesis catalysts useful in the present invention may be a metal compound-containing catalyst or non-metal compound-containing catalyst or mixtures thereof. Preferred are the metal-compound containing catalysts, particularly the metal oxide catalysts.

Metal-Compound Containing Catalysts

A wide range of metal compound-containing catalysts and catalyst supports may be used in the present invention.

Representative metal compound-containing catalysts are refractory materials and include the compounds of the Group I-A, II-A, III-A, IV-B or actinide series metals. Representative compounds include the carbide, nitride, boride or oxide of a Group I-A, II-A, III-A, IV-B or actinide series metal, used alone or in combination.

The catalyst must be thermally stable under the operating condition in the reaction zones and are preferably particulate in form. The carbides of the Groups I-A, II-A, III-A, IV-B and actinide series metals are particularly preferred because it is believed that the carbide metal compound-containing catalyst are the most stable under the severe reaction conditions of the present invention. Preferably, the catalyst can also be regenerated by the periodic burning-off of any undesirable deposits such as coke. The regeneration of catalyst by the burning off coke is well known in the catalyst and petroleum processing art.

Representative Group I-A metal compound-containing catalyst include the carbide, nitride, boride, oxide of lithium, sodium, potassium, rubidium, and cesium. Most preferred among the Group I-A metals is lithium.

Representative Group II-A metal compound-containing catalysts include the carbide, nitride, boride, or oxide of beryllium, magnesium, calcium, strontium, barium, and radium. Most preferred among the Group II-A metals is calcium.

Representative Group III-A metal compound-containing catalysts include the carbide, nitride, boride, or oxide of aluminum, scandium, yttrium, lanthanum, and actinium. Most preferred among the Group III-A metals is aluminum.

Representative Group IV-B metal compound-containing catalysts include the carbide, nitride, boride, or oxide of titanium, zirconium, hafnium, and zirconium. Most preferred among the Group IV-B metals is zirconium. Representative actinide series metal compound-containing catalysts include the carbide, nitride, boride, or oxide of thorium and uranium. Most preferred among the actinide series metals is thorium.

A particularly preferred catalyst for use in the present invention is thorium oxide on alumina.

Non-Metal Compound Containing Catalysts

Representative non-metal compound containing catalysts are catalysts containing compounds of boron and silicon.

Representative boron compound containing catalysts are refractory materials and include boron carbide, or boron nitride. Particularly preferred is boron nitride.

Representative silicon compound-containing catalysts are refractory materials and include silicon carbide, nitride, silicon boride or silicon oxide. Particularly preferred is silicon carbide.

The advantages of the present invention will be readily apparent from a consideration of the following examples.

EXAMPLES

The Table below gives the results for runs with and without added aluminum vapor. The aluminum vapor was added to the reaction gas by passing hydrogen over molten aluminum metal. Except for the added aluminum vapor, the reaction gas consisted of 87.5 methane, 5% ethane and 7.5% hydrogen. The reaction temperature was 1100° C. and the space velocity was 18,000 $hr^{-1}$. The catalyst used consisted of $ThO_2/Al_2O_3$: Fused white alumina refractory bubbles, obtained from the Carborundum Company were crushed and sieved and the fraction 8–20 mesh used in preparing this catalyst. To 354.5 gr of the crushed and sieved refractory bubbles was added a solution of 43.6 gr $Th(NO_3)_4 \cdot H_2O$ in 70.9 ml of distilled water. Small portions of the solution were added with continuous stirring. The wet slurry was placed in the flask of a Rotovac apparatus, and ammonia vapors passed over the mixture while the flask was rotated. Thorium hydroxide was precipitated on the support by this procedure. Even dispersion was maintained by the flask rotation. The mixture was first dried under a heat lamp in a stream of nitrogen, then calcined in air at 1000° C. for 3 hrs.

The apparatus and procedures used for obtaining the data in Table I was substantially the same as described in our U.S. Pat. No. 4,567,331, the disclosure of which is incorporated herein by reference, with the following exceptions:

(1) A large diameter reactor tube ($\frac{3}{4}''$ O.D. × $\frac{1}{2}''$ I.D.) was used. A central thermowell was inserted in the reactor. The temperature of the catalyst bed was measured at its midpoint, using a platinum/platinum—10% rhodium thermocouple.

(2) The measurement of coke for data in Table I was carried out as follows: Upon completion of a run to determine catalyst activity and selectivity, the feed was replaced by argon. Air was then added to the argon flow to an extent of 20% by volume. In the meantime, the trapping and sampling system at the reactor exit had been replaced by a CO converter and Ascarite traps to permit estimation of CO formed by reaction of oxygen in the air/argon mixture with coke on the catalyst. Dilute air was used until the temperature maximum, produced by the exothermic coke/oxygen reaction, was past. Then the argon flow was terminated, and 100% air was used at a flow rate equal to the feed flow to assure similar mass transport conditions. By these means, complete combustion of the coke on catalyst was obtained. Weighing the Ascarite absorption tube before and after use afforded the weight of CO absorbed, from which the carbon content of the catalyst was readily calculated. Appropriate tests were performed to determine that the CO converter was functioning, and that carbon combustion was complete;

(3) In the calculation of aromatics, heavy hydrocarbons, and coke for the data in Table I, it was assumed that the carbon atoms from converted methane, and the carbon atoms from converted ethane, were uniformly distributed among all the products. Thus, the proportion of carbon atoms in benzene that resulted from methane conversion was the carbon atoms in total product benzene times the fraction $$\frac{\text{(carbon atoms from converted methane)}}{\text{(carbon atoms from converted methane + carbon atoms from converted ethane)}}.$$

Calculation of moles or weight of benzene formed was then straight forward, from the stoichiometric relationships. Similarly calculations were made for the other aromatic compounds and for coke. Finally, heavy hydrocarbon was calculated as the difference in the carbon atoms from converted methane (minus carbon atoms in the aromatics from converted methane plus carbon atoms in coke from converted methane). This difference was multiplied by 13.02 to obtain the weight of heavy hydrocarbon. Assuming a molecular weight of 13.02 corresponds to an assumption that the heavy hydrocarbons have a molecular formula of $(CH)_x$. This is correct to within a few percent. Gas chromatographic analysis of the heavy hydrocarbon collected in the traps showed that about 95% of the heavy hydrocarbon was useful product;

(4) In Table I, the % yield was calculated as follows:

$$\% \text{ Yield} = \frac{(\text{Wt of Useful Products from CH}_4) \times 100}{\text{Wt of Methane Converted}}$$

Useful products include (1) the aromatics (benzene, toluene and the xylenes) and (2) the heavy hydrocarbons (polynuclear aromatic hydrocarbons containing 4 and fewer fused rings).

It was assumed that the two to four carbon hydrocarbons formed as products were being recycled as feed to the process. The 5% ethane in the feed used in the experiments recorded in Table I simulated this situation. Thus the 5% ethane in the feed essentially corre- sponds to the two to four carbon hydrocarbons content of the process feed at steady state operation in a reactor in which these products are recycled to the feed.

TABLE I

| | | | | Results | | |
| --- | --- | --- | --- | --- | --- | --- |
| | | | | Fraction of carbon converted, appearing as | | |
| Run No. | Al Vapor (ppm) | Conv. mole % of CH$_4$ fed | Yield | Aromatics | Heavy Hydro-carbons | Coke |
| 1 | none | 27 | 52 | 0.15 | 0.51 | .34 |
| 2 | .04 | 28 | 55 | 0.14 | 0.57 | .29 |

The above data illustrates one preferred embodiment of the invention and the increased yield of higher molecular weight hydrocarbons by the addition of a small but effective amount of aluminum metal vapor added to the feed gas. Similarly, the above data indicates a significant decrease in the formation of coke.

What is claimed is:

1. In a continuous catalyst process for the production of higher molecular weight hydrocarbons from lower molecular weight hydrocarbons in which a lower molecular weight hydrocarbon containing reaction gas is contacted in a reaction zone with a higher molecular weight hydrocarbon synthesis catalyst under $C_{2+}$ hydrocarbon synthesis conditions, the improvement comprising increasing production of higher molecular weight hydrocarbons by the addition of an effective amount of aluminum metal vapor to the reaction gas, said synthesis conditions including a temperature greater than 1000° C. and a gas hourly space velocity of greater than 3200 hr$^{-1}$ and wherein said hydrocarbon synthesis catalyst contains a carbide, nitride, boride or oxide of a Group I-A, II-A, III-A, IV-B or actinide series metal.

2. The process of claim 1 wherein said reaction zone contains a stationary or fluidized bed of said catalyst.

3. The process of claim 2 wherein said temperature is in the range of 1100° to 1200° C., said space velocity is in the range of 6000 to 36,000 hr$^{-1}$ and at least 20 mole percent of said lower molecular weight hydrocarbons is converted to higher molecular weight hydrocarbons.

4. The process of claim 3 wherein said aluminum metal vapor comprises 0.01 to 110 parts per million of the reaction gas.

5. The process of claim 4 wherein said catalyst contains a Group I-A metal selected from lithium, potassium or cesium.

6. The process of claim 4 wherein said catalyst contains a Group II-A metal selected from beryllium, magnesium, calcium, strontium, barium or radium.

7. The process of claim 4 wherein said catalyst contains a Group III-A metal selected from aluminum, scandium, yttrium, lanthanum and actinium.

8. The process of claim 4 wherein said catalyst contains a Group IV-B metal selected from titanium, zirconium, and hafnium.

9. The process of claim 1 wherein said catalyst contains thorium or uranium.

10. The process of claim 1 wherein said catalyst contains a boron compound.

11. The process of claim 1 wherein said catalyst contains a silicon compound.

12. The process of claim 4 wherein said aluminum metal vapor comprises 0.02 to 0.5 parts per million of said reaction gas.

13. In a continuous catalytic process for the production of higher molecular weight hydrocarbons from lower molecular weight hydrocarbons in which a lower molecular weight hydrocarbon containing reaction gas is contacted in a reaction zone with a higher molecular weight hydrocarbon synthesis catalyst under $C_{2+}$ hydrocarbon synthesis conditions, improvement comprising increasing the production of higher molecular weight hydrocarbons by the addition of an effective amount of aluminum metal vapor to the reaction gas, said synthesis conditions including a temperature in the range of 1150° to 1175° C., a space velocity is in the range of 9000 to 18,000 hr$^{-1}$ and wherein at least 40 mole percent of said lower molecular weight hydrocarbons is converted to higher molecular weight hydrocarbons and wherein said hydrocarbon synthesis catalyst contains a carbide, nitride, boride or oxide of a Group I-A, II-A, III-A, IV-B or actinide series metal.

14. The process of claim 13 wherein said catalyst contains a compound of a Group I-A metal selected from lithium, potassium or cesium.

15. The process of claim 13 wherein said catalyst contains a compound of a Group II-A metal selected from beryllium, magnesium, calcium, strontium, barium or radium.

16. The process of claim 13 wherein said catalyst contains a compound of a Group III-A metal selected from aluminum, scandium, yttrium, lanthanum and actinium.

17. The process of claim 13 wherein said catalyst contains a compound of a Group IV-B metal selected from titanium, zirconium, and hafnium.

18. The process of claim 13 wherein said catalyst contains a compound of thorium or uranium.

19. The process of claim 13 wherein said catalyst contains a boron compound.

20. The process of claim 13 wherein said catalyst contains a silicon compound.

21. The process of claim 4 wherein said aluminum metal vapor comprises 0.03 to 0.1 parts per million of said reaction gas.

22. In a continuous catalytic process for the production of higher molecular weight hydrocarbons from lower molecular weight hydrocarbons in which a lower molecular weight hydrocarbon containing reaction gas is contacted in a reaction zone with a higher molecular weight hydrocarbon synthesis catalyst under $C_{2+}$ hydrocarbon synthesis conditions, the improvement comprising increasing the production of higher molecular weight hydrocarbons by the addition of 0.02 to 0.5 parts per million of aluminum metal vapor to the reaction gas, said synthesis conditions including a temperature in the range of 1150° to 1175° C., a space velocity is in the range of 9000 to 18,000 hr$^{-1}$, said catalyst contains an oxide of a Group I-A, II-A, III-A, IV-B or actinide series metal and wherein at least 40 mole percent of said lower molecular weight hydrocarbons is converted to higher molecular weight hydrocarbons.

* * * * *